United States Patent
Konstantino et al.

(10) Patent No.: US 9,233,234 B2
(45) Date of Patent: Jan. 12, 2016

(54) BALLOON CATHETER WITH IMPROVED COLUMN STRENGTH AND TORQUE TRANSMISSION

(75) Inventors: Eitan Konstantino, Orinda, CA (US); Jayson De Los Santos, Pinole, CA (US); Tanhum Feld, Moshav Merhavya (IL)

(73) Assignee: TRIREME MEDICAL, LLC, Pleasanton, CA (US)

( * ) Notice: Subject to any disclaimer, the term of this patent is extended or adjusted under 35 U.S.C. 154(b) by 285 days.

(21) Appl. No.: 13/087,169

(22) Filed: Apr. 14, 2011

(65) Prior Publication Data

US 2012/0095397 A1     Apr. 19, 2012

Related U.S. Application Data

(60) Provisional application No. 61/324,654, filed on Apr. 15, 2010.

(51) Int. Cl.
*A61M 25/10* (2013.01)
*A61M 25/00* (2006.01)
*A61M 25/06* (2006.01)

(52) U.S. Cl.
CPC ......... *A61M 25/104* (2013.01); *A61M 25/0043* (2013.01); *A61M 25/10* (2013.01); *A61M 25/0068* (2013.01); *A61M 25/0069* (2013.01); *A61M 2025/0063* (2013.01); *A61M 2025/0681* (2013.01); *A61M 2025/1081* (2013.01); *A61M 2025/1093* (2013.01)

(58) Field of Classification Search
CPC ................ A61M 25/0069; A61M 2025/0063; A61M 2025/00681; A61M 2025/1093; A61M 2025/1081

USPC ................... 604/96.01, 103, 103.03, 103.04, 604/164.03; 606/192, 194

See application file for complete search history.

(56) References Cited

U.S. PATENT DOCUMENTS

| 4,456,000 A | 6/1984 | Schjeldahl et al. |
| 4,819,751 A | 4/1989 | Shimada et al. |
| 5,246,420 A | 9/1993 | Kraus et al. |
| 5,827,231 A | 10/1998 | Harada |

(Continued)

FOREIGN PATENT DOCUMENTS

| CN | 101505822 A | 8/2009 |
| EP | 0339093 A1 | 11/1989 |

(Continued)

OTHER PUBLICATIONS

International search report and written opinion dated Jul. 12, 2011 for PCT/US2011/032752.

(Continued)

*Primary Examiner* — Nathan R Price
(74) *Attorney, Agent, or Firm* — Wilson Sonsini Goodrich & Rosati

(57) ABSTRACT

A balloon catheter capable of delivering torque and pushing through obstructions includes a relatively weak balloon segment of a catheter and rotatable asymmetric tip. A reinforcement sleeve increases column strength and torque transmission to push the balloon and rotate the tip to facilitate passage through said obstructions. The tip is preferably asymmetric around its axis, usually being beveled, and the reinforcement slide includes a slide lock mechanism which increases shaft flexibility after balloon deployment.

12 Claims, 5 Drawing Sheets

(56) References Cited

U.S. PATENT DOCUMENTS

| | | |
|---|---|---|
| 5,868,779 A | 2/1999 | Ruiz |
| 6,030,405 A | 2/2000 | Zarbatany et al. |
| 6,066,157 A | 5/2000 | Barbere |
| 7,022,106 B2 | 4/2006 | Jorgensen et al. |
| 7,273,470 B2 | 9/2007 | Wantink |
| 7,491,213 B2 | 2/2009 | Perreault et al. |
| 7,635,347 B2 | 12/2009 | Kastenhofer |
| 2005/0070847 A1 | 3/2005 | Van Erp et al. |
| 2006/0129176 A1 | 6/2006 | Griffin et al. |
| 2009/0156998 A1 | 6/2009 | Arana et al. |
| 2009/0187143 A1 | 7/2009 | Vreeman |
| 2012/0116490 A1 | 5/2012 | Wesselmann et al. |

FOREIGN PATENT DOCUMENTS

| | | |
|---|---|---|
| JP | 2005013710 A * | 1/2005 |
| WO | WO 2006/135581 A2 | 12/2006 |
| WO | WO 2007/094374 A1 | 8/2007 |

OTHER PUBLICATIONS

European search report and opinion dated Oct. 23, 2013 for EP Application No. 11769703.7.

Co-pending U.S. Appl. No. 14/801,852, filed Jul. 17, 2015.

* cited by examiner

BALLOON CATHETER WITH IMPROVED COLUMN STRENGTH AND TORQUE TRANSMISSION

CROSS-REFERENCES TO RELATED APPLICATIONS

This application claims the benefit of provisional application No. 61/324,654, filed on Apr. 15, 2010, the full disclosure of which is incorporated herein by reference.

BACKGROUND OF THE INVENTION

1. Field of the Invention

This disclosure relates to the field of medical devices, specifically to the use and structure of balloon angioplasty or dilatation catheters.

Despite being in widespread use for over 20 years and substantial development efforts, the delivery of angioplasty balloons to a target lesion in a patient's vasculature is often a challenge. During delivery, the operator often has to overcome tortuous anatomy, long and calcified lesions (especially in peripheral arteries) and tight turns. Further difficulties can arise from the need to cross previously treated lesions where restenosis has occurred.

Balloon catheters are usually delivered over a guide wire that is inserted into the vasculature and through the target lesion prior to advancement of the balloon catheter. With most balloon catheters, the operator controls advancement by pushing/pulling the catheter shaft from over the guide wire. During delivery, the operator will push the catheter shaft over the guide wire until the balloon reaches the target lesion. When encountering an obstacle, the operator can pull back and push again forcefully in the hope that the balloon catheter will overcome this obstacle. Some catheters have improved torque transmitting capabilities but these are limited and work best in short balloons.

In conventional balloon catheter constructions, at least at a distal segment of the shaft near the balloon is made from a relatively soft polymer material which is very ineffective for transmitting pushing force and torque to the catheter tip, typically relying on the stiffness of the guide wire which is often insufficient. The balloon region of a balloon catheter is made of a very thin folded balloon; it is the weakest in terms of push force and torque. The distal section of the balloon is attached to the catheter's guide wire lumen at the very distal end of the catheter, and to the catheter distal shaft (but only to the inflation lumen and not to its internal concentric guide wire lumen) on its proximal balloon taper. Therefore this segment of the catheter has inefficient structural integrity in delivering the push force to the catheter tip in attempt to overcome an obstacle.

The difficulties described above are exacerbated in catheters having long balloons, such as those used in peripheral arteries. Such balloons can reach or exceed 30 cm in length. Further difficulty arises in peripheral arteries when attempting to cross the iliac arch where wire bending may occur as the push force is not effectively transferred to the distal part of the catheter. Attempts to reinforce the catheters using metallic inner members or stiff members have failed since the catheter must be flexible in order to travel through the arteries without damaging the vessels. Other limitations to reinforcing the balloon include the need to keep a low profile (minimize the addition of new materials or layers of tubing) and the need to have short inflation/deflation times (maximizing the area of the inflation lumen to allow rapid liquid flow into the balloon during inflation and out of the balloon during deflation).

Thus, the ability of balloon catheters and especially balloon catheters with long balloons used to treat peripheral arteries (with balloon lengths up to 30 cm) to reach and cross target lesions is often limited and can prolong procedures requiring the use of excessive contrast media and radiation, both of which can be harmful to the patient.

For all of the above reasons, it would be desirable to provide improved angioplasty balloon catheters and methods for their use. In particular, it would be desirable if the balloon catheters could have improved pushability or column strength, particularly over their distal regions comprising the balloon, as well as improved torqueability, and thus be capable of being advanced through tortuous regions of the vasculature and through restricted, difficult-to-pass vascular lesions. In addition to possessing such improved column strength and torsional stiffness, it is desirable that the flexibility of the distal region of the catheter, particularly that comprising a balloon, remain sufficiently high to that the balloon remains sufficiently conformable to be delivered around tight bends and through tortuous regions of the vasculature. At least some of these objectives will be met by the inventions described below.

2. Description of the Background Art

Patents describing balloon angioplasty catheter constructions include U.S. Pat. Nos. 7,491,213; 7,635,347; 7,273,470; 7,022,106; 6,030,405; and 5,827,231.

BRIEF SUMMARY OF THE INVENTION

This invention discloses a balloon catheter with improved ability to deliver torque and push throughout the device, including the relatively weak balloon segment of a catheter, to the distal end of the catheter. The balloon catheter typically includes a rotatable asymmetric tip and a reinforced shaft with an improved ability to transmit torque to rotate and realign a leading edge of the tip to facilitate passage through an obstruction. The tip is preferably asymmetric around its axis, usually being beveled, and the reinforced catheter shaft is capable of transmitting rotation and push force to the catheter tip while maintaining flexibility and deployment performance. When an obstacle is encountered rotation of the catheter allows the tip to pass through the obstacle.

A particularly advantageous feature of the present invention is referred to as a "slide lock mechanism" which provides intra-balloon support while maintaining flexibility and uniform inflation. This can be achieved through extending a support lumen thru the inflatable part of the balloon to fit inside or close to the distal balloon leg. Attempts to provide full intra-balloon support tubes which are anchored at both ends to the catheter can cause the balloon to deform and assume a non-cylindrical configuration when fully inflated (as shown in FIG. 2). By decoupling the two ends of the balloon from the shaft while providing support tube throughout the full length of the balloon, as achieved with the present invention, such balloon deformation can be avoided. The particular slide lock mechanism of the present invention is also able to provide for both increased column strength (catheter pushability) and torsional rigidity (the ability to rotate the proximal end of the catheter shaft about its axis and cause a comparable rotation of the distal end of the shaft even when the shat is passing through tortuous regions of the vasculature), which are advantageous in catheter placement. Increased column strength and torsional rigidity allow improved transmission of both turning and translation of the shaft from the proximal end so that such motions are accurately reflected in the distal end of the catheter and can allow crossing of tight, long and diffuse lesions that currently are very difficult to treat and may eventually lead to amputation.

In a first aspect of the present invention, the balloon catheter comprises a shaft having an inner member a proximal end, a distal end, and a guide wire lumen extending therethrough. When the guide wire lumen extends fully through the inner member, the catheter will have an "over-the-wire" configuration where the guide wire passes through the entire length of the catheter. When the guide wire lumen passes through only a portion of the inner member or other structure of the shaft, the catheter can have a "rapid exchange" configuration where only a short length of the guide wire, typically from 10 cm to 35 cm, is received through the catheter and passes through the catheter balloon.

The catheter will further include a distal tip disposed at the distal end of the catheter shaft. The tip could be symmetric or the distal tip will have an asymmetric configuration, typically being beveled at an angle in the range from 30 degrees to 60 degrees, usually being about 45 degrees, so that a leading edge of the tip can be oriented relative to a luminal obstruction to facilitate passing that obstruction. Usually, the distal tip will be a separate component attached to a distal end of the inner member of the catheter shaft. In other instances, particularly when a distal end is not beveled, a distal tip may be formed integrally in the inner member or other portion of the shaft itself.

The balloon catheter of the present invention further comprises a reinforcement sleeve which is disposed coaxially over the inner member. The reinforcement sleeve has a proximal end and a distal end and, when in place over the inner member, provides an annular inflation lumen between an outer surface of a shaft and inner wall of the sleeve.

The balloon catheter further includes an inflatable balloon, typically a non-distensible balloon formed of a conventional balloon material such as nylon or pebax or other materials known in the arts. The balloon has a distal end and a proximal end where the distal end is secured directly or indirectly to the distal tip and/or to the distal end of the inner member. The proximal end of the balloon is secured to the reinforcement sleeve, typically near the distal end of the reinforcement sleeve. As at least the distal end of the reinforcement sleeve will be free to move relative to the inner member, as described in more detail below, the distal end of the balloon will be able to move relative to the proximal end of the balloon as the balloon is inflated, reducing the risk that the balloon will deform from the desired cylindrical configuration as it is inflated.

In the preferred constructions, a distal end of the extended outer shaft will directly couple or engage the distal tip of the catheter when the balloon is deflated and the catheter is being advanced through the vasculature. By engaging or otherwise being coupled to the distal tip, the reinforcement sleeve is able to transmit both axial force (i.e., increase the overall column strength of the catheter) as well as torsional force from the proximal end of the catheter to the distal end. The enhanced column strength and torsional rigidity are achieved during the catheter advancement, which is when they are most needed. Moreover, the torsional rigidity and column strength of the reinforcement sleeve are provided in addition to the strength and rigidity of the catheter shaft itself so that the overall column strength and torsional rigidity are the sum of the contributions of each component.

While the distal end of the reinforcement sleeve will engage or otherwise be coupled to the distal tip (or the distal end of the balloon) while the balloon is deflated during catheter advancement, the reinforcement sleeve will not be attached to the catheter tip so that the reinforcement sleeve will be able to move or retract in a proximal direction in response to balloon elongation when the balloon is inflated. Thus, two ends of the balloon will be able to move apart from each other and the stress on the balloon which would result from the balloon ends being anchored is eliminated. Thus, the balloon will be able inflate with less risk of the deformation than if the balloons were both attached to the balloon shaft.

The distal end or region of the reinforcement sleeve will have one or more ports or passages formed therethrough in order to permit balloon inflation. An inflation medium can be introduced into the annular lumen between the sleeve and the shaft, typically through an inflation port on a proximal hub of the catheter. The inflation medium can travel the length of the catheter through the annular lumen. The distal region of the sleeve may be generally cylindrical so that the annular lumen continues the entire length of the catheter to reach the distal tip. With such a fully extending sleeve, the inflation ports can be formed along the length of the sleeve at multiple locations within the balloon. Alternatively, in order to produce the crossing profile of the balloon, the sleeve can be tapered so that it lies immediately over the outer surface of the distal end of the inner member, thus eliminating the inflation medium over a distal region of the balloon. In such cases, the holes will need to be located in the proximal area of the balloon before the out shaft if fully tapered.

The inner member may have any conventional angioplasty balloon shaft structure, typically comprising a hypotube or other metal body portion over at least a portion of its length. Alternatively, the inner member could be a polymeric body over at least a portion of its length, typically being reinforced with a braid, mesh, embedded wires, or the like, in order to increase column strength and torsional rigidity.

The reinforcement sleeve will typically comprise a polymer tube over at least a portion of its length, where the polymer may be reinforced with meshes, braids, wires, or the like, in order to increase both its column strength and torsional rigidity.

In a specific embodiment of the catheter, the balloon will include at a distal constriction (distal leg) which does not inflate with introduction of the inflation medium. This distal restriction is spaced apart from the inner member so that a channel is created which receives the distal end of the reinforcement sleeve. Usually, the channel will be sufficiently long so that the reinforcement sleeve remains in the channel even when it is fully retracted in its proximal direction when the balloon is fully inflated.

In a second aspect, the present invention provides a method for dilatating a body lumen, typically dilatating a lesion in a blood vessel. The method comprises providing a catheter having an inner member, a distal tip (area distally to the inflatable balloon), a reinforcement sleeve (outer shaft), and an inflatable balloon connected at a distal end to the inner member and at a proximal end to the reinforcement sleeve. The catheter is advanced through a patient's vasculature by pushing a proximal end of the catheter shaft to transmit a push force to the distal tip of the catheter through both the inner member and the reinforcement sleeve. While the catheter is being advanced by pushing, the distal ends of the both the inner member and the outer shaft remain engaged against the distal tip of the catheter in order to facilitate positioning of the balloon at the lesion or other target site. Once at the lesion or other target site, the balloon is inflated so that the balloon radially expands and elongates. As the balloon elongates, the reinforcement sleeve separates from the distal tip to accommodate such balloon elongation, whereby stresses and constricting forces which could deform the balloon are greatly reduced. Usually, while a balloon is being advanced, it is also being rotated, where the rotational torque is transmitted to the distal tip through both the inner member and the reinforcement sleeve, both of which remain engaged against the tip during catheter advancement. Usually, the distal will have a beveled or other asymmetric end which may be reoriented relative to an obstruction in the vasculature in order to help pass the obstruction as the catheter is advanced and rotated.

In another aspect of the present invention, the catheter inner member may utilize reinforced tubes allowing rotation and push force transmission. This reinforcement is achieved by use of braided shafts where a braid of thin metallic or polymer ribbons that increase the inner member torque and push force transmission without compromising the shafts flexibility. The braided shafts can be the external shaft or the internal shaft (inner member) or both. The internal shaft is connected to the balloon distal end and the external shaft is connected to the balloon proximal end, often these two are not connected. Reinforcing those shafts, especially the inner shaft, greatly improves the operators control over the balloon throughout the catheters length all the way to the tip, mainly torque and pushability.

In yet another aspect of the present invention, the catheter shaft may utilize reinforced tubes or support material in the internal shaft, and/or external shafts and the two are connected at an anchoring area near the proximal end of the balloon, allowing enhanced control of the balloon by the operator.

In still another aspect of the present invention, an inner construction of the balloon comprises a continuation of the distal shaft/inflation lumen that extends through the balloon all the way to the balloon distal leg or tip. This elongated distal shaft could be bonded at the balloon distal end or can be stabilized by pressure applied from the balloon leg. To provide effective inflation/deflation the inflation lumen that extends throughout the balloon contains holes, openings or cavities underlining the balloon section to allow for inflation medium such as saline or saline's mix to reach and inflate the balloon.

DETAILED DESCRIPTION OF THE INVENTION

The following description will describe various aspects of the invention. Embodiments of this invention relate to a balloon catheter with improved rotational torque and column strength that reach through the balloon and to the tip of the catheter, providing improved obstacle crossing capabilities. This design allows for better control of the catheter by the operator. The embodiments relate to treatment of occlusions in blood vessels (both coronary and peripheral) but can also find use in treating other body lumens such as the urinary and reproductive systems.

Figure 1:
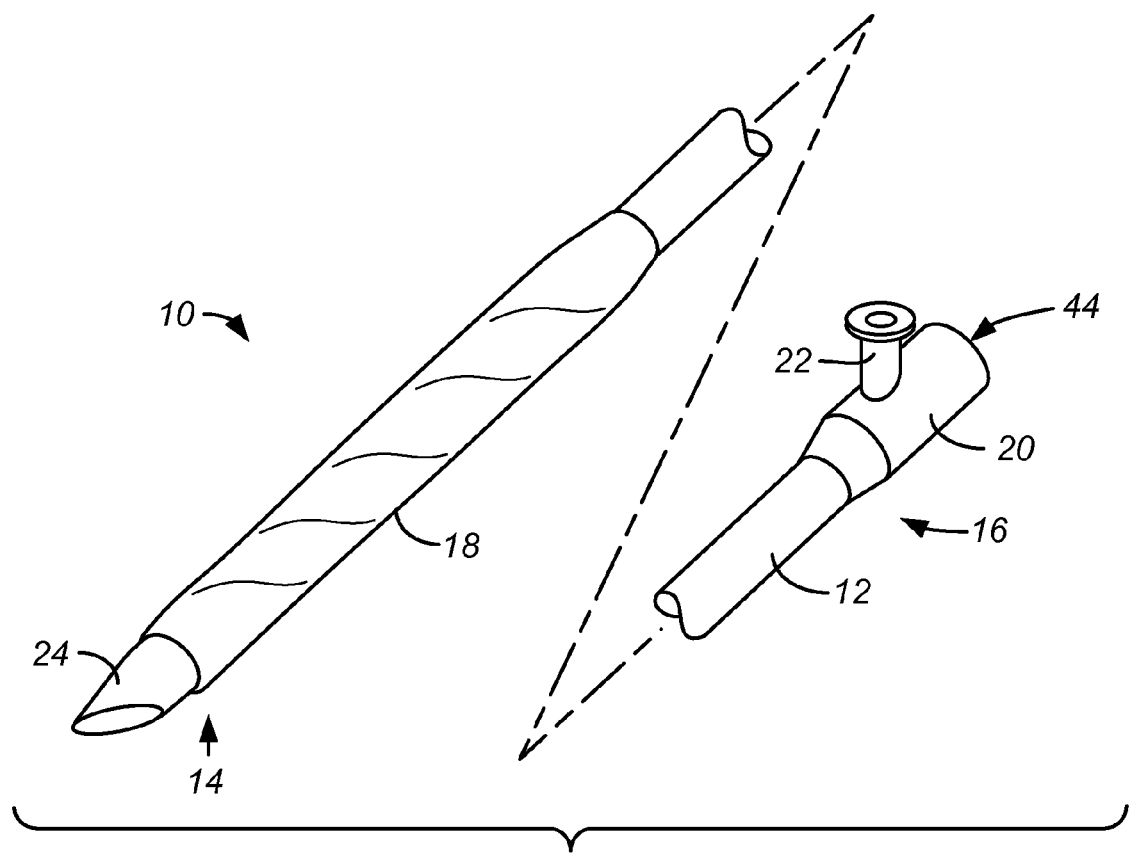
FIG. 1 illustrates a balloon catheter of the type which may incorporate the slide lock of the present invention.
Figure 2:
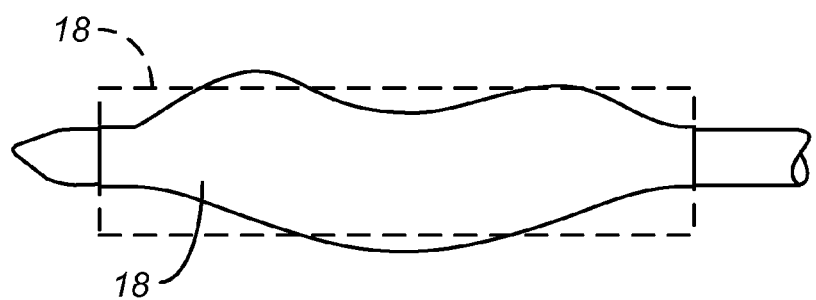
FIG. 2 illustrates a prior art balloon with internal reinforcement which has been inflated without the slide lock mechanism of the present invention where the balloon profile becomes deformed.

Referring now to FIG. 1, a balloon catheter 10 of the type which may employ the slide lock mechanism of the present invention comprises a shaft assembly 12 having a distal end 14 and a proximal end 16. An inflatable balloon 18 is mounted on a distal region of the shaft assembly 12, and will have dimensions selected based on its intended use. For example, in treating long lesions of the peripheral vasculature, the balloon will typically have a length exceeding 10 cm, often exceeding 20 cm, and in some instances approximately 30 cm. In balloon catheters without the slide lock mechanism in the present invention, where both ends of the balloon are attached to the shaft assembly which holds the end at a fixed distance, the balloon 18 when inflated may become deformed, as shown in full line in FIG. 2. By employing the slide lock mechanism of the present invention, however, the balloon will typically inflate to a more perfect cylindrical configuration, as shown in broken line in FIG. 2.

Figure 3A:
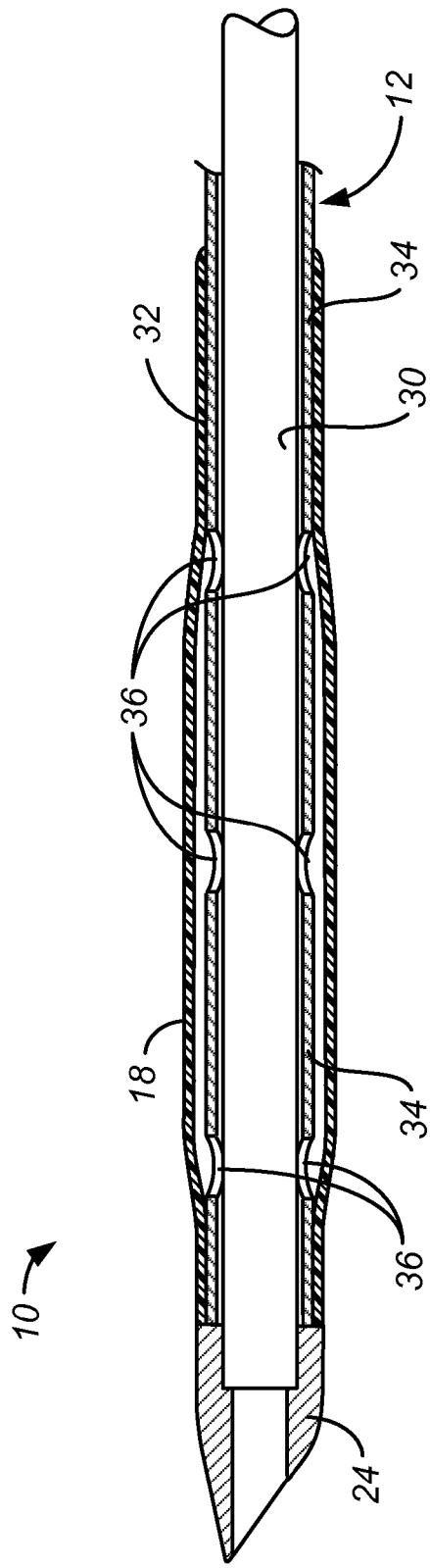
FIGS. 3A-3C illustrate a first embodiment of a balloon catheter employing the slide lock mechanism of the present invention where the reinforcement sleeve has a generally constant diameter along its entire length.
Figure 3B:
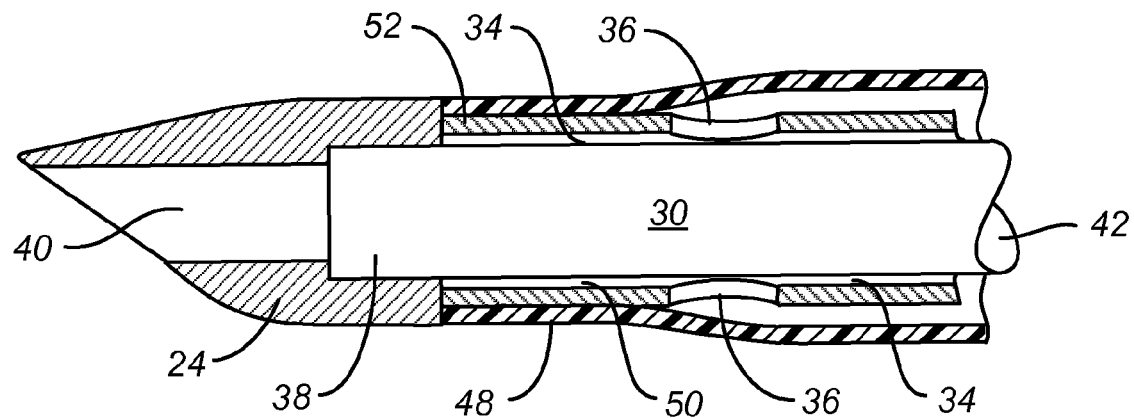
Figure 3C:
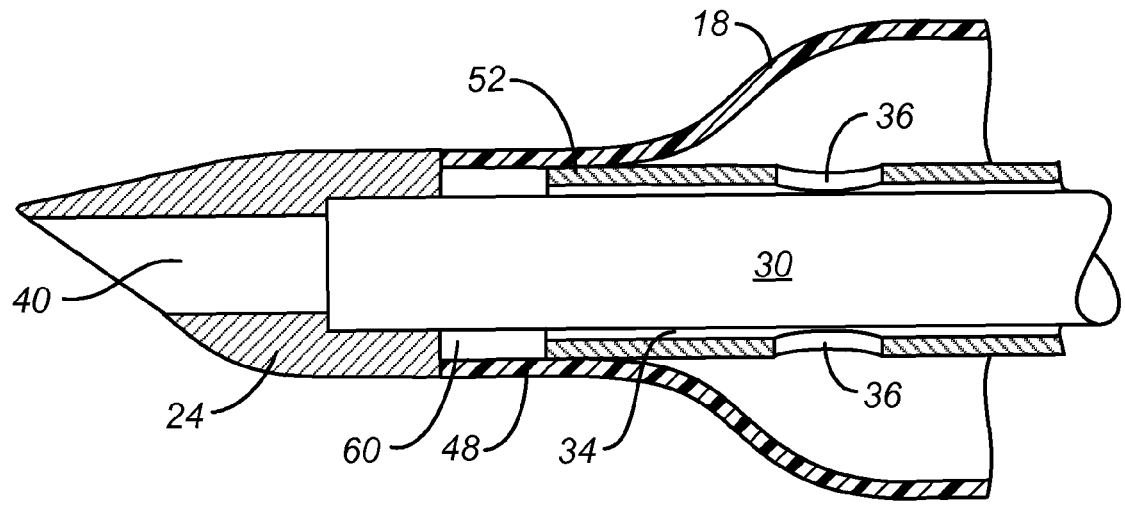

Reference is made to FIGS. 3A-3C which provide a schematic representation of an extended distal shaft extending throughout the balloon. The extended distal shaft or reinforcement member (also described as torque transmission member, a push transmission member, or a buckling resistant member) extends to the distal part of the balloon. This reinforcement member can be made of braided or conventional polymer and will be able to transfer the push and torque forces to the tip of the balloon. Since this reinforcement member also provides the inflation lumen, a distal portion of the member inside the balloon will be customized with holes, slits, and voids or alike to accommodate balloon inflation and deflation. The elongated distal shaft can be bonded to the balloon distal leg or tip. Preferably, the elongated member can be inserted and held in place by pressure and/or friction applied from the balloon distal leg by using dimensional fit but it can also extend all the way to the distal balloon area without pressure fit or special dimensional fit. The pressure and friction forces improve transfer of push and torque forces to the distal section of the balloon.

The catheter 10 illustrated in FIGS. 3A-3C comprises a shaft assembly 12 including an inner member 30 and a coaxially disposed reinforcement sleeve 32. The reinforcement sleeve 32 is cylindrical along its entire length having generally constant diameter such an annular inflation lumen 34 is defined between an outer surface of the inner member 30 and an inner wall of the reinforcement sleeve 32. The annular inflation lumen 34 extends the entire length from inflation port 22 on proximal hub 20 of the balloon catheter 10 (FIG. 1) to the distal tip 24. The inflation medium can be released into the region beneath balloon 18 through a plurality inflation port 36 located along the length of the reinforcement sleeve 32 beneath the balloon.

Referring now in particular to FIGS. 3B and 3C, at all times, at distal end 38 of the inner member 30 is fixedly attached to a proximal side of the distal tip 24. An opening or port 40 formed through the distal tip 24 opens into a hollow lumen 42 of the inner shaft 30 in order to receive a guidewire which can be passed into the lumen through a guidewire port 44 on the proximal hub 20 (FIG. 1).

The balloon 18 has a constricted region or collar 48 at it's distal end (and typically also at its proximal end) which is fixedly attached to the proximal end or surface of the distal tip 24 such that the balloon is sealed to the tip to provide containment of the inflation medium within the lumen. Collar 48 defines an annular channel 50 between the collar and outer surface of the inner member 30, and it is within this channel that the distal end 52 of the reinforcement sleeve 32 passes and engages the proximal end of distal tip 24. The distal end 52 of the reinforcement sleeve 32 is not, however, attached to the distal tip 24, but it will remain engaged against the tip so long as the balloon remains uninflated. Upon balloon inflation, however, the distal end 52 of the reinforcement sleeve 32 will be drawn approximately to cause a gap 60 between the distal end and the proximal end of the distal tip 24, as shown in FIG. 3C. This gap is caused by movement of the sleeve 32 relative to the inner member 30 which in turn is caused by elongation of the balloon 18 as it is inflated. The length of the gap 60 will thus generally correspond to the magnitude of the balloon elongation, typically being at least several millimeters, often being in the range from 0.5 cm to 5 cm, usually being in the range from 1 cm to 3 cm.

By comparing the configurations of FIGS. 3B and 3C, it can be seen that while the balloon is uninflated and the catheter is being advanced, the enforcement sleeve 32 engages the distal tip 24 and can thus enhance both the column strength and the torsional rigidity of the catheter so that movement of the proximal end of the catheter can be faithfully transmitted to the distal tip. In contrast, when the balloon 18 is inflated at the target site or lesion, as illustrated in FIG. 3C, the annular gap which is created enhances the flexibility and the conformability of the catheter and in particular reduces the risk of balloon deformation which is a principal objective of the present invention.

Figure 4A:
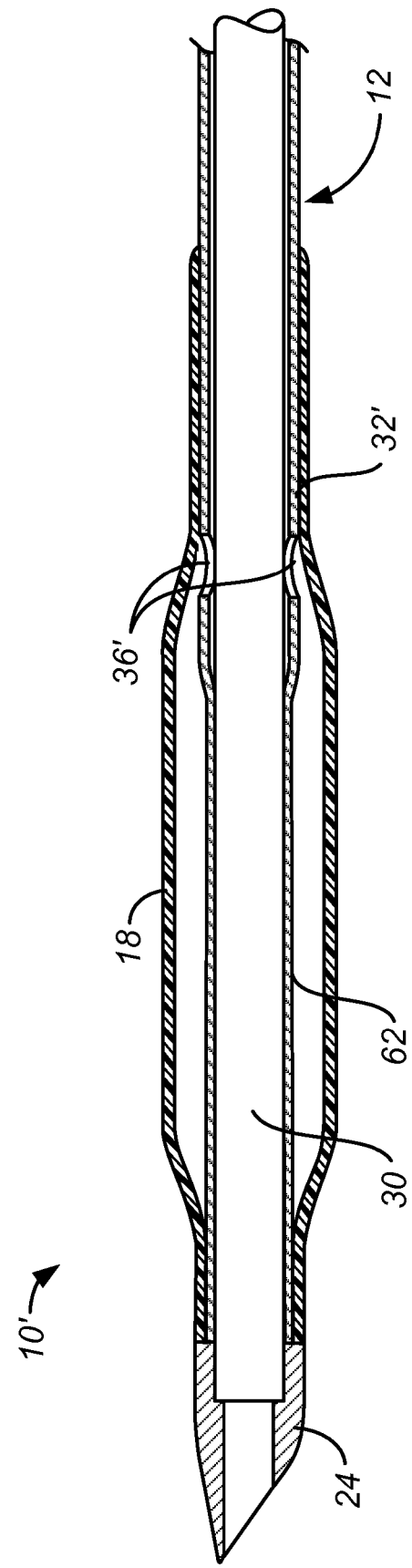
FIGS. 4A-4C illustrate a second embodiment of a catheter construction employing the slide lock mechanism of the present invention where a reinforcement sleeve has a tapered distal end.
Figure 4B:
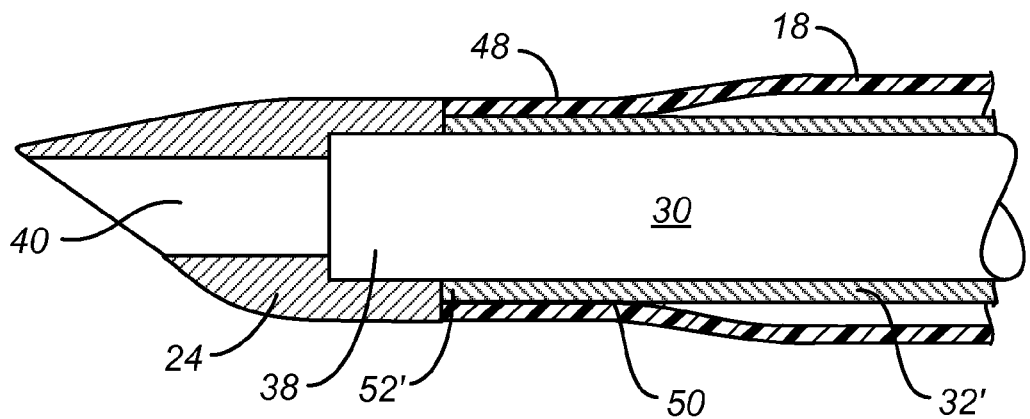
Figure 4C:
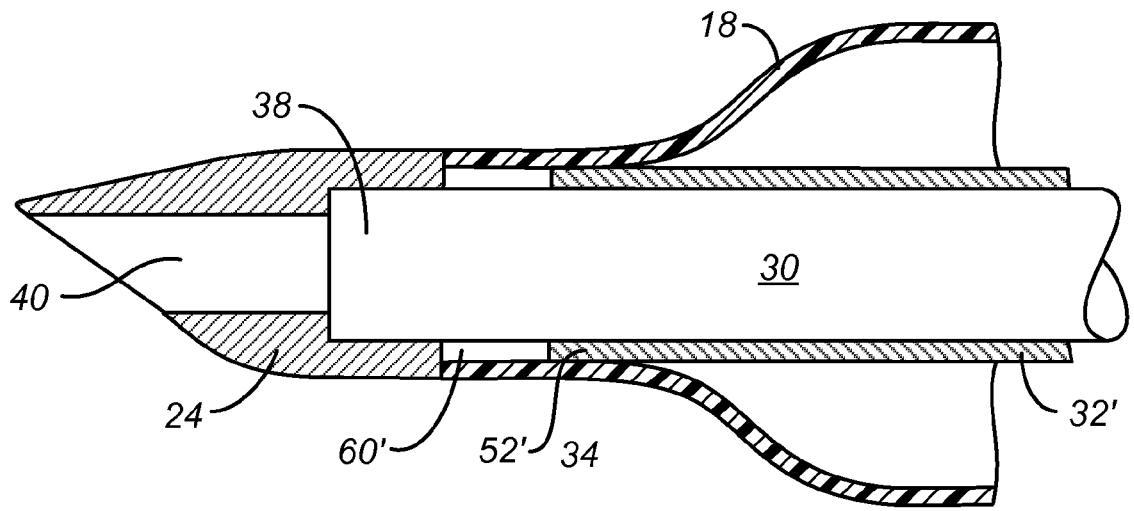

FIG. 4A-4C illustrate a preferred embodiment of the elongated distal shaft described in the previous paragraph. In this embodiment the distal shaft is tapered to the inner member allowing a smaller diameter and reducing balloon profile. Thus the balloon will have better crossing capabilities without compromising push and torque force transfer. In this case since the distal shaft is tapered the holes are located in the tapered area to allow liquid or gas to flow and enable balloon inflation. Another type of reinforcing member can be metallic wire or ribbon that help support the inner member of the balloon during delivery while providing flexibility. In such case inflation holes may not be required.

As illustrated in FIGS. 4A-4C, the catheter 10' is identical in all respects to the catheter 10 except that reinforcement sleeve 32' is tapered and has a smaller diameter over a region 62 which lies beneath lumen 18 and over inner-shaft 30. Note that all identical components will be given identical reference numbers in both FIGS. 3A-3C and FIGS. 4A-4C. By reducing the diameter of the distal region 62 of the sleeve 32', typically so that it has an inner diameter which is greater than the outer diameter of inner member 30 by distance sufficient only to allow sliding of the sleeve 32' over the inner member 30, the crossing profile of the catheter can be significantly reduced.

The tapering of the distal region 62 also changes the distal engagement configuration of the distal end 52' of the reinforcement sleeve 32' and the tip 24, as best seen in FIGS. 4B and 4C. In particular, the distal end 52' of the reinforcement sleeve 32' will be sandwiched between the distal color region 48 of the balloon 18 prior to balloon inflation, as best seen in FIG. 4B. The diameter of the distal tip 24 and the collar region 48 of the balloon 18 can be correspondingly decreased. As the distal end of the 52' of the reinforcement sleeve 32' is proximally retracted upon balloon inflation, as shown in FIG. 4C, the gap 60' will also have a reduced width relative to the gap 60 of catheter 10 as shown in FIG. 3C. Other operational characteristics of the catheter 10' will generally be identical to those of the catheter 10.

Figure 5A:
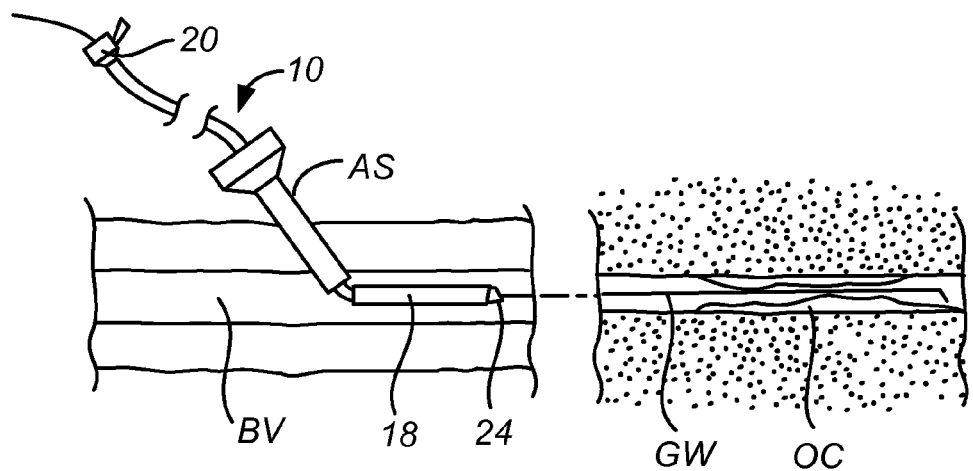
FIGS. 5A-5C illustrate use of the balloon catheter of the present invention for dilating a lesion in a blood vessel.
Figure 5B:
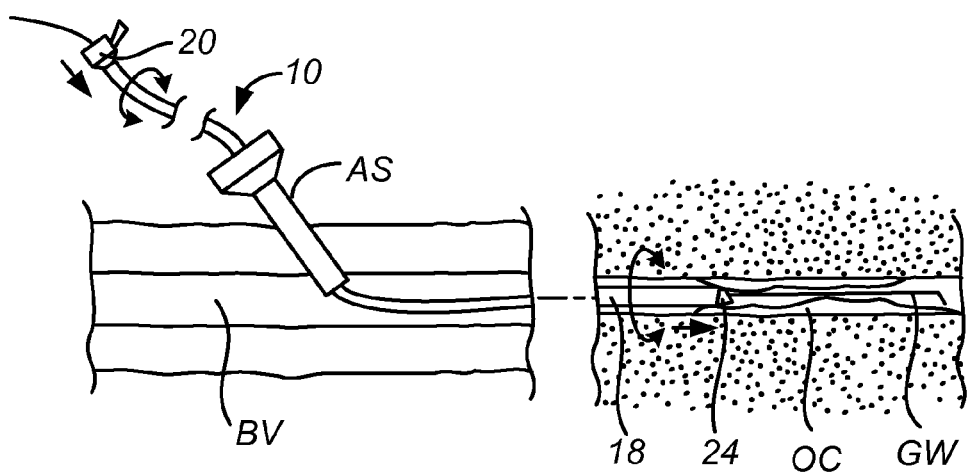
Figure 5C:
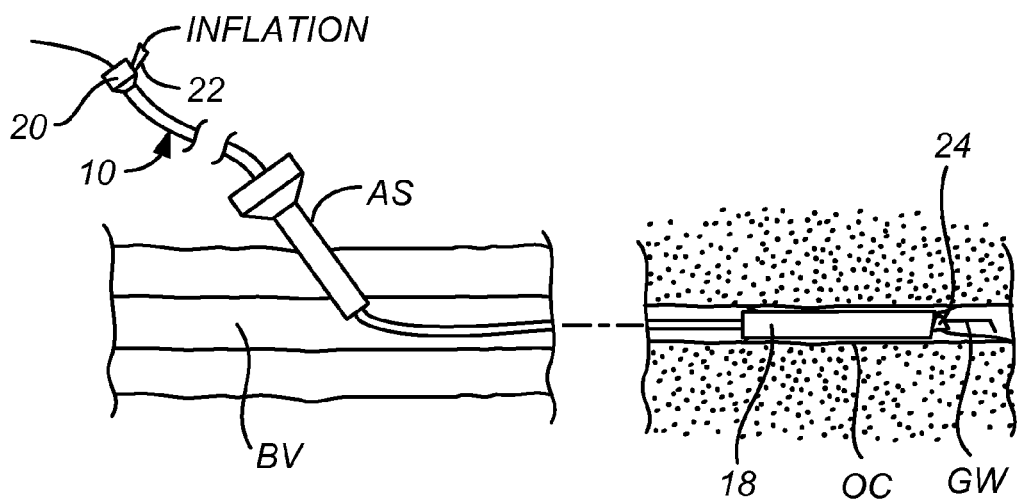

Referring now to FIGS. 5A-5C, catheter 10 may be introduced to a blood vessel BV by any conventional technique, including surgical cut down. Usually, however, the catheter 10 will be introduced by the Seldinger technique through an access sheath AS so that the balloon 18 enters the blood vessel BV over a guidewire GW. The intent is to advance the balloon 18 until it reaches an occlusive site OS at a region in the vasculature which is typically remote from the access site. The occlusion site OS may be in the peripheral vasculature, the coronary vasculature, or elsewhere. Long balloons having lengths over 10 cm, often over 20 cm, will often find greatest use in the peripheral blood vessels.

After initial introduction, the catheter 10 will be advanced through the vasculature until the balloon 18 reaches occlusive site OS, as illustrated in FIG. 5B. During the advancement, however, of the present invention allows the catheter to be both pushed and rotated, as shown by the arrows in FIG. 5B, to facilitate advancement of the distal tip of the catheter past intermediate occlusions and through tortuousities. Usually, the distal tip 24 will have a beveled or otherwise asymmetric tip which has a leading edge which may be reoriented to facilitate passing through or past occlusions. The enhanced torsional strength and rigidity of the present invention make axially advancing and rotating the distal tip of the catheter much easier than would otherwise be the case in the absence of the reinforcement structure.

As shown in FIG. 5C, after reaching the occlusion site OS, the balloon 18 is inflated by introducing inflation medium through the port 22 on hub 20. The slide lock mechanism in the present invention, as described in detail above, allows the balloon 18 to inflate with a reduced tendency to deform so that the fully inflated profile is in a preferred cylindrical configuration.

The significance of having the reinforcement sleeve not bonded distally (or proximally, or discontinued at any point along its length in a manner that will deliver push, torque or resist buckling) can be explained as follows. During inflation the balloon inflates both in radial and longitudinal directions, i.e. the one of the "side effects" of the balloon inflation is the fact that the balloon also lengthen during inflation. Typically, the balloon length can lengthen 5%-15% relatively to its diameter depending on its material, wall thickness, length, pressure and other factors. For example, 20 cm length balloon can grow approximately 10 mm in length during inflation and in extreme cases can grow 30 mm in length. Since the reinforcement sleeve is stiffer than the balloon thin wall and typically does not grow as much during inflation, the member constrains the balloon from growing axially and as a result the balloon shape changes. The balloon may obtain a "banana" shape," an "S" shape, or other non-cylindrical shapes. This phenomenon is undesired and may affect the balloon performance and its affect of the vessel wall by adding undesired forces that contribute to vessel trauma. Keeping the reinforcement member unbound and unattached in a manner that will allow the balloon to lengthen without constraint (e.g. weak bond that can detached or similar mechanisms) allows for the balloon to inflate without significant constraint from the shaft. However, the reinforcing member will not deliver as much force if it is not extended all the way to the distal balloon end and have physical interaction enabling force and/or torque transmission. Therefore, "clutch" mechanism that can transmit forces during delivery and crossing lesions but can allow unconstrained inflation of the balloon is desirable.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A balloon catheter comprising:
   an inner member having a proximal end, a distal end, and a guidewire lumen extending therethrough;
   a distal tip at the distal end of the inner member;
   a reinforcement sleeve disposed coaxially over the inner member, said sleeve having a proximal end and a distal end and providing an inflation lumen between an outer surface of the inner member and an inner wall of the sleeve;
   an inflatable balloon having a distal end secured to the distal tip and a proximal end secured to the reinforcement sleeve so that the balloon can receive an inflation medium from the inflation lumen, the inflatable balloon further having a distal leg proximal of the distal end and a distal taper proximal of the distal leg;
   wherein, when the balloon is deflated, the distal end of the reinforcement sleeve is held in place by pressure and/or friction applied from the distal leg and will engage a proximal surface of the distal tip to transfer pushing forces to said tip,
   wherein, when the balloon is inflated, the distal end of the reinforcement sleeve can separate from the proximal surface of the distal tip to enhance flexibility and limit deformation of the inflated balloon, and
   wherein the distal end of the balloon is attached to the proximal surface of the distal tip.

2. A balloon catheter as in claim 1, wherein the distal end of the distal tip is asymmetrically beveled so that the distal tip can be rotationally oriented relative to a luminal obstruction when the catheter is present in a body lumen.

3. A balloon catheter as in claim 1, wherein a distal region of the reinforcement sleeve is tapered within the balloon to reduce the crossing profile of the balloon.

4. A balloon catheter as in claim 1, wherein the reinforcement sleeve has a substantially uniform diameter over a distal region.

5. A balloon catheter as in claim 1, wherein the inner member comprises a hypotube over at least a portion of its length.

6. A balloon catheter as in claim 1, wherein the inner member comprises a polymer tube over at least a portion of its length.

7. A balloon catheter as in claim 6, wherein polymer tube is reinforced.

8. A balloon catheter as in claim 1, wherein the reinforcement sleeve comprises a polymer tube over at least a portion of its length.

9. A balloon catheter as in claim 8, wherein the polymer tube is reinforced.

10. A balloon catheter as in claim 1, wherein the balloon has a distal construction which defines an annular channel which receives the distal end of the reinforcement sleeve.

11. A balloon catheter as in claim 1, wherein the distal tip is a separate component attached to the distal end of the inner member.

12. A balloon catheter as in claim 1, wherein the balloon has a collar region at its distal end which is attached to the distal tip.

* * * * *